US009855404B2

(12) United States Patent
Romoscanu

(10) Patent No.: US 9,855,404 B2
(45) Date of Patent: Jan. 2, 2018

(54) DUAL BEND RADII STEERING CATHETER

(71) Applicant: St. Jude Medical International Holding S.À.R.L., Luxembourg (LU)

(72) Inventor: Alexandre Ioan Romoscanu, Geneva (CH)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 1046 days.

(21) Appl. No.: 14/011,286

(22) Filed: Aug. 27, 2013

(65) Prior Publication Data

US 2014/0330251 A1 Nov. 6, 2014

Related U.S. Application Data

(60) Provisional application No. 61/819,216, filed on May 3, 2013.

(51) Int. Cl.
*A61M 25/01* (2006.01)
*A61B 18/14* (2006.01)

(52) U.S. Cl.
CPC ..... *A61M 25/0147* (2013.01); *A61B 18/1492* (2013.01); *A61M 25/0138* (2013.01)

(58) Field of Classification Search
CPC .......... A61M 25/0138; A61M 25/0147; A61M 25/0144; A61M 2025/0161; A61M 2025/015; A61B 1/00078; A61B 1/0057; A61B 2017/00323; A61B 1/0055; A61B 1/0056; A61B 2017/00327
See application file for complete search history.

(56) References Cited

U.S. PATENT DOCUMENTS

| 2,515,366 A | | 7/1950 | Zublin |
| 3,416,531 A | | 12/1968 | Edwards |
| 3,557,780 A | | 1/1971 | Sato |
| 3,572,325 A | * | 3/1971 | Bazell et al. ........ A61B 1/0055 138/120 |
| 3,583,393 A | | 6/1971 | Takahashi |
| 3,700,289 A | | 10/1972 | Billinski et al. |
| 3,710,781 A | | 1/1973 | Huthcins |

(Continued)

FOREIGN PATENT DOCUMENTS

| EP | 0980693 A1 | 2/2000 |
| EP | 2749214 A1 | 7/2014 |

(Continued)

*Primary Examiner* — Kami A Bosworth
(74) *Attorney, Agent, or Firm* — Dykema Gossett PLLC

(57) ABSTRACT

A bi-directional steerable catheter that, for a given tip deflection angle, generates a first articulation radius in a first lateral direction and a second articulation radius in a second lateral direction, the second articulation radius being different than the first articulation radius. The catheter includes two pull wire portions that can be individually and selectively put under tension to cause deflection of the tip in a corresponding lateral direction. Actuation of a first of the pull wire portions causes a shift in the neutral axis of the catheter over a portion of the steering section, resulting in articulation over a shorter length of the steering section and thus a smaller bend radius. Actuation of a second of the pull wire portions does not result in a neutral axis shift, so that articulation is over substantially the entire length of the steering section, resulting in a larger bend radius.

17 Claims, 4 Drawing Sheets

(56) References Cited

U.S. PATENT DOCUMENTS

| | | |
|---|---|---|
| 3,739,770 A | 6/1973 | Muri |
| 3,799,151 A | 3/1974 | Fukaumi et al. |
| 3,802,440 A | 4/1974 | Salem et al. |
| 3,905,361 A | 9/1975 | Hewson et al. |
| 3,948,255 A | 5/1976 | Davidson |
| 3,998,216 A | 12/1976 | Hosono |
| 4,108,211 A | 8/1978 | Tanaka |
| 4,329,980 A | 5/1982 | Terada |
| 4,351,323 A | 9/1982 | Ouchi et al. |
| 4,432,349 A | 2/1984 | Oshiro |
| 4,502,482 A | 3/1985 | DeLuccia et al. |
| 4,516,972 A | 5/1985 | Samson |
| 4,543,090 A | 9/1985 | McCoy |
| 4,580,551 A | 4/1986 | Siegmund et al. |
| 4,586,923 A | 5/1986 | Gould et al. |
| 4,601,705 A | 7/1986 | McCoy |
| 4,612,927 A | 9/1986 | Krüger |
| 4,664,113 A | 5/1987 | Frisbie et al. |
| 4,700,693 A | 10/1987 | Lia et al. |
| 4,723,936 A | 2/1988 | Buchbinder et al. |
| 4,753,223 A | 6/1988 | Bremer |
| 4,771,788 A | 9/1988 | Millar |
| 4,834,069 A | 5/1989 | Umeda |
| 4,850,351 A | 7/1989 | Herman et al. |
| 4,874,371 A | 10/1989 | Comben et al. |
| 4,886,067 A | 12/1989 | Palermo |
| 4,898,577 A | 2/1990 | Badger et al. |
| 4,940,062 A | 7/1990 | Hampton et al. |
| 4,960,134 A | 10/1990 | Webster |
| 4,960,410 A | 10/1990 | Pinchuk |
| 4,960,411 A | 10/1990 | Buchbinder |
| 4,998,916 A | 3/1991 | Hammerslag et al. |
| 4,998,923 A | 3/1991 | Samson et al. |
| 5,030,204 A | 7/1991 | Badger et al. |
| 5,056,517 A | 10/1991 | Fenici |
| 5,108,368 A | 4/1992 | Hammerslag et al. |
| 5,114,414 A | 5/1992 | Buchbinder |
| 5,125,895 A | 6/1992 | Buchbinder et al. |
| 5,152,744 A | 10/1992 | Krause et al. |
| 5,178,129 A | 1/1993 | Chikama et al. |
| 5,190,050 A | 3/1993 | Nitzsche |
| 5,203,772 A * | 4/1993 | Hammerslag ..... A61M 25/0144 600/585 |
| 5,228,441 A * | 7/1993 | Lundquist ......... A61B 18/1492 600/380 |
| 5,242,430 A | 9/1993 | Arenas et al. |
| 5,299,562 A | 4/1994 | Heckele et al. |
| 5,304,131 A | 4/1994 | Paskar |
| 5,308,324 A | 5/1994 | Hammerslag et al. |
| 5,315,996 A | 5/1994 | Lundquist |
| 5,318,525 A | 6/1994 | West et al. |
| 5,322,064 A | 6/1994 | Lundquist |
| 5,327,905 A | 7/1994 | Avitall |
| 5,329,923 A | 7/1994 | Lundquist |
| 5,358,479 A | 10/1994 | Wilson |
| 5,364,351 A | 11/1994 | Heinzelman et al. |
| 5,368,564 A | 11/1994 | Savage |
| 5,383,852 A | 1/1995 | Stevens-Wright |
| 5,383,923 A | 1/1995 | Webster, Jr. |
| 5,394,864 A | 3/1995 | Kobayashi et al. |
| 5,395,327 A | 3/1995 | Lundquist et al. |
| 5,395,328 A | 3/1995 | Lundquist et al. |
| 5,397,304 A | 3/1995 | Truckai |
| 5,409,000 A | 4/1995 | Imran |
| 5,431,168 A | 7/1995 | Webster, Jr. |
| 5,437,288 A | 8/1995 | Schwartz et al. |
| 5,441,483 A | 8/1995 | Avitall |
| 5,448,989 A | 9/1995 | Heckele |
| 5,454,787 A | 10/1995 | Lundquist |
| 5,456,664 A | 10/1995 | Heinzelman et al. |
| 5,462,527 A | 10/1995 | Stevens-Wright et al. |
| 5,477,856 A | 12/1995 | Lundquist |
| 5,478,330 A | 12/1995 | Imran et al. |
| 5,484,407 A | 1/1996 | Osypka |
| 5,487,757 A | 1/1996 | Trukai et al. |
| 5,507,725 A | 4/1996 | Savage et al. |
| 5,531,686 A | 7/1996 | Lundquist et al. |
| 5,545,200 A | 8/1996 | West et al. |
| 5,562,619 A | 10/1996 | Mirarchi et al. |
| 5,564,615 A | 10/1996 | Bishop et al. |
| 5,573,520 A | 11/1996 | Schwartz et al. |
| 5,603,697 A | 2/1997 | Grundy et al. |
| 5,605,543 A | 2/1997 | Swanson |
| 5,611,777 A | 3/1997 | Bowden et al. |
| 5,656,029 A | 8/1997 | Imran et al. |
| 5,662,662 A | 9/1997 | Bishop et al. |
| 5,676,653 A | 10/1997 | Taylor et al. |
| 5,685,868 A | 11/1997 | Lundquist |
| 5,702,433 A | 12/1997 | Taylor et al. |
| 5,715,817 A | 2/1998 | Stevens-Wright et al. |
| 5,728,144 A | 3/1998 | Edwards et al. |
| 5,741,429 A | 4/1998 | Donadio, III et al. |
| 5,743,876 A | 4/1998 | Swanson |
| 5,749,828 A | 5/1998 | Solomon et al. |
| 5,779,669 A | 7/1998 | Haissaguerre et al. |
| 5,782,239 A | 7/1998 | Webster, Jr. |
| 5,782,828 A | 7/1998 | Chen et al. |
| 5,791,350 A | 8/1998 | Morton |
| 5,797,842 A | 8/1998 | Pumares et al. |
| 5,797,905 A | 8/1998 | Fleischman et al. |
| 5,807,241 A | 9/1998 | Heimberger |
| 5,820,591 A | 10/1998 | Thompson et al. |
| 5,823,955 A | 10/1998 | Kuck et al. |
| 5,824,031 A | 10/1998 | Cookston et al. |
| 5,827,278 A | 10/1998 | Webster, Jr. |
| 5,833,632 A | 11/1998 | Jacobsen et al. |
| 5,857,046 A | 1/1999 | Barkus et al. |
| 5,861,024 A | 1/1999 | Rashidi |
| 5,865,800 A | 2/1999 | Mirarchi et al. |
| 5,879,295 A | 3/1999 | Li et al. |
| 5,881,727 A | 3/1999 | Edwards |
| 5,882,333 A | 3/1999 | Schaer et al. |
| 5,897,529 A | 4/1999 | Ponzi |
| 5,897,554 A | 4/1999 | Chia et al. |
| 5,904,667 A | 5/1999 | Falwell |
| 5,910,129 A | 6/1999 | Koblish et al. |
| 5,911,720 A | 6/1999 | Bourne et al. |
| 5,916,214 A | 6/1999 | Cosio et al. |
| 5,931,811 A | 8/1999 | Haissaguerre et al. |
| 5,935,102 A | 8/1999 | Bowden et al. |
| 5,944,690 A | 8/1999 | Falwell et al. |
| 5,954,746 A | 9/1999 | Holthaus et al. |
| 5,967,978 A | 10/1999 | Littmann et al. |
| 6,004,279 A | 12/1999 | Crowley et al. |
| 6,013,052 A | 1/2000 | Durman et al. |
| 6,027,473 A | 2/2000 | Ponzi |
| 6,027,863 A | 2/2000 | Donadio, III |
| 6,033,394 A | 3/2000 | Vidlund et al. |
| 6,047,700 A | 4/2000 | Eggers et al. |
| 6,048,339 A | 4/2000 | Zirps et al. |
| 6,063,080 A | 5/2000 | Nelson et al. |
| 6,064,905 A | 5/2000 | Webster, Jr. et al. |
| 6,096,036 A | 8/2000 | Bowe et al. |
| 6,107,004 A | 8/2000 | Donadio, III |
| 6,120,520 A | 9/2000 | Saadat et al. |
| 6,156,034 A | 12/2000 | Cosio et al. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,224,587 B1 | 5/2001 | Gibson |
| 6,241,728 B1 | 6/2001 | Gaiser et al. |
| 6,251,104 B1 | 6/2001 | Kesten et al. |
| 6,254,568 B1 | 7/2001 | Ponzi |
| 6,263,224 B1 | 7/2001 | West |
| 6,267,746 B1 | 7/2001 | Bumbalough |
| 6,221,070 B1 | 8/2001 | Tu et al. |
| 6,270,496 B1 | 8/2001 | Bowe et al. |
| 6,394,976 B1 | 5/2002 | Winston et al. |
| 6,408,889 B1 * | 6/2002 | Komachi ............. A61B 1/0055 138/120 |
| 6,428,489 B1 | 8/2002 | Jacobsen et al. |
| 6,440,088 B1 | 8/2002 | Jacobsen et al. |
| 6,468,260 B1 | 10/2002 | Bumbalough et al. |

(56) References Cited

U.S. PATENT DOCUMENTS

| | | |
|---|---|---|
| 6,470,205 B2 | 10/2002 | Bosselmann et al. |
| 6,500,167 B1 | 12/2002 | Webster, Jr. |
| 6,522,933 B2 | 2/2003 | Nguyen |
| 6,533,783 B1 | 3/2003 | Töllner |
| 6,551,271 B2 | 4/2003 | Nguyen |
| 6,551,302 B1 | 4/2003 | Rosinko et al. |
| 6,569,114 B2 | 5/2003 | Ponzi et al. |
| 6,571,131 B1 | 5/2003 | Nguyen |
| 6,582,430 B2 | 6/2003 | Hall |
| 6,585,717 B1 | 7/2003 | Wittenberger et al. |
| 6,585,718 B2 | 7/2003 | Hayzelden et al. |
| 6,599,304 B1 | 7/2003 | Selmon et al. |
| 6,602,278 B1 | 8/2003 | Thompson et al. |
| 6,641,528 B2 | 11/2003 | Torii |
| 6,652,506 B2 | 11/2003 | Bowe et al. |
| 6,663,588 B2 | 12/2003 | DuBois et al. |
| 6,695,808 B2 | 2/2004 | Tom |
| 6,758,830 B1 | 7/2004 | Schaer et al. |
| 6,776,765 B2 | 8/2004 | Soukup et al. |
| 6,783,510 B1 | 8/2004 | Gibson et al. |
| 6,837,867 B2 | 1/2005 | Kortelling |
| 6,866,662 B2 | 3/2005 | Fuimaono et al. |
| 6,890,329 B2 | 5/2005 | Carroll et al. |
| 6,893,436 B2 | 5/2005 | Woodard et al. |
| 6,913,594 B2 | 7/2005 | Coleman et al. |
| 6,926,669 B1 | 8/2005 | Stewart et al. |
| 6,955,675 B2 | 10/2005 | Jain |
| 7,008,401 B2 | 3/2006 | Thompson et al. |
| 7,011,655 B2 | 3/2006 | Thompson et al. |
| 7,081,114 B2 | 7/2006 | Rashidi |
| 7,099,717 B2 | 8/2006 | Woodard et al. |
| 7,211,063 B2 | 5/2007 | Tom |
| 7,232,422 B2 | 6/2007 | Gibson et al. |
| 7,276,062 B2 | 10/2007 | McDaniel et al. |
| 7,285,108 B2 | 10/2007 | Koerner et al. |
| 7,300,438 B2 | 11/2007 | Falwell et al. |
| 7,301,131 B2 | 11/2007 | Gauthier et al. |
| 7,311,705 B2 | 12/2007 | Sra |
| 7,331,958 B2 | 2/2008 | Falwell et al. |
| 7,344,543 B2 | 3/2008 | Sra |
| 7,371,232 B2 | 5/2008 | Scheib |
| 7,387,626 B2 | 6/2008 | Edwards et al. |
| 7,387,630 B2 | 6/2008 | Mest |
| 7,402,151 B2 | 7/2008 | Rosemann et al. |
| 7,415,300 B2 | 8/2008 | Anderson et al. |
| 7,419,080 B2 | 9/2008 | Smith et al. |
| 7,465,300 B2 | 12/2008 | Arless et al. |
| 7,524,301 B2 | 4/2009 | Dubois et al. |
| D599,904 S | 9/2009 | Anderson |
| 7,625,617 B1 | 12/2009 | Anderson et al. |
| 7,629,015 B2 | 12/2009 | Anderson et al. |
| 7,731,682 B2 | 6/2010 | Bencini et al. |
| 7,824,345 B2 | 11/2010 | Euteneuer et al. |
| 7,881,769 B2 | 2/2011 | Sobe |
| 7,914,466 B2 | 3/2011 | Davis et al. |
| 7,951,165 B2 | 5/2011 | Golden et al. |
| 8,007,462 B2 | 8/2011 | Gibson et al. |
| 8,257,344 B2 | 9/2012 | Ponzi et al. |
| 2005/0049574 A1 | 3/2005 | Petrick et al. |
| 2006/0200000 A1* | 9/2006 | Sato et al. ........... A61B 1/0055 600/146 |
| 2006/0200047 A1* | 9/2006 | Galdonik .......... A61M 25/0138 600/585 |
| 2006/0270976 A1 | 11/2006 | Savage et al. |
| 2007/0270679 A1* | 11/2007 | Nguyen ............ A61M 25/0043 600/373 |
| 2010/0152574 A1 | 6/2010 | Erdman et al. |
| 2010/0280449 A1 | 11/2010 | Alvarez et al. |
| 2010/0280525 A1* | 11/2010 | Alvarez .......... A61B 17/00234 606/130 |
| 2010/0298638 A1 | 11/2010 | Slater |
| 2011/0251519 A1 | 10/2011 | Romoscanu |
| 2012/0089125 A1 | 4/2012 | Scheibe et al. |
| 2014/0088356 A1* | 3/2014 | Matsuo et al. ....... A61B 1/0056 600/109 |

FOREIGN PATENT DOCUMENTS

| | | |
|---|---|---|
| JP | H11262530 A | 9/1999 |
| WO | 01/85246 A1 | 11/2001 |

* cited by examiner

DUAL BEND RADII STEERING CATHETER

RELATED APPLICATION

This application claims the benefit of U.S. Provisional Patent Application No. 61/819,216, filed May 3, 2013, the disclosure of which is hereby incorporated by reference in its entirety.

FIELD OF THE DISCLOSURE

The present disclosure is directed generally to catheter assemblies, and more specifically to catheter assemblies having deflectable distal tips for manipulation and steering.

BACKGROUND

Many steering catheter designs exist which are capable of deflecting the distal end of a catheter in various ways using a control handle. In one form of steering catheters, a control handle is coupled with a pull wire or wires in an arrangement that applies or releases tension in the pull wire(s) as the plunger or steering mechanism is manipulated, thereby causing a controlled deflection of the distal tip of the catheter. Controlled deflection is in a single direction in some steering catheters, and is bi-directional in other applications.

For bi-directional applications, one design challenge is to allow for sufficient range and control of movements with controls which are not unduly complicated. In many devices, rather elaborate designs have been attempted which are not sufficiently simple, effective, and easy to use.

A steering catheter that provides a desirable and diverse range of deflection movement with a simple and easy to operate internal structure would be welcome.

SUMMARY

Various embodiments of the disclosure include a bidirectional steering catheter that provides lateral deflection control of the distal end of a catheter system in two directions where each direction of bending deflection is associated with a different bend radius. In various embodiments, such dual bending is made possible through use of a single compression coil disposed only in a segment of the steering section of the catheter. The design can enable easier assembly and with fewer components than conventional bidirectional steering catheters, and can also provide a reduced profile than conventional bidirectional steering catheters.

Structurally, a catheter assembly in accordance with the present disclosure includes a shaft portion and a steering portion. The shaft portion has a proximal end and a distal end and including a shaft section sidewall that defines a central lumen. The steering portion having a proximal end and a distal end, the proximal end of the steering portion being operatively coupled with the distal end of the shaft portion. The steering portion includes a steering section sidewall having a first steering section sidewall lumen and a second steering section sidewall lumen formed therein. The catheter assembly defines a central axis that passes through the proximal end of the shaft portion and the distal end of the steering portion, the shaft portion and the steering portion being substantially concentric about the central axis. A uni-directional stiffening member can be operatively coupled to the steering section sidewall proximate the first steering section sidewall lumen and over a standoff length of the steering section, the uni-directional stiffening member defining a uni-directional bending portion of the steering section and an offset axis that is radially offset from and substantially parallel to the central axis.

A first pull wire portion extends through the central lumen and the first steering section sidewall lumen such that actuation of the first pull wire portion causes deflection of the steering portion in a first lateral direction, the first pull wire portion being routed proximate the uni-directional stiffening member. During actuation of the first pull wire portion, a neutral axis of the catheter assembly along the uni-directional bending portion is proximate the offset axis such that a first bend radius of the steering section is defined for a steering angle $\alpha$.

A second pull wire portion extends through the central lumen and the second steering section sidewall lumen such that actuation of the second pull wire portion causes deflection of the steering portion in a second lateral direction. In one embodiment, the second lateral direction is different than the first lateral direction. During actuation of the second pull wire portion, a neutral axis of the catheter assembly along the uni-directional bending portion is proximate the central axis such that a second bend radius of the steering section is defined for the same steering angle $\alpha$, the second steering radius being greater than the first steering radius.

In one embodiment, the first sidewall lumen is rotationally offset from the second sidewall lumen. The first steering section sidewall lumen can be diametrically opposed to the second steering section sidewall lumen. A transition piece can optionally extend partially into the shaft portion and partially into the steering portion. Also, the first pull wire portion and the second pull wire portion can be e two separate pull wires, or can be portions of the same wire that is looped through the catheter assembly.

In one embodiment, the uni-directional stiffening member is a compression coil. In one non-limiting example, the compression coil has an outer diameter of about 0.42 mm and an inner diameter of about 0.26 mm. In another non-limiting example, the compression coil is formed of a 0.003 inch by 0.010 inch rectangular section wire. The compression coil can be configured so as not to delaminate from the first steering section sidewall lumen. In one embodiment, a compressibility ratio of the compression coil relative to the steering section sidewall is at least 1:5.

In some embodiments, the shaft section sidewall defines a first shaft sidewall passageway and a second shaft sidewall passageway formed therein, the first shaft sidewall passageway and the second shaft sidewall passageway extending parallel to the central axis over at least a portion of the shaft portion and passing through the distal end of the shaft portion. In one embodiment, the first shaft sidewall passageway is axially aligned with the first steering section sidewall lumen, and the second shaft sidewall passageway is axially aligned with the second steering section sidewall lumen. In this embodiment, the first pull wire portion and the second pull wire portion can pass through the first shaft sidewall passageway and the second shaft sidewall passageway, respectively.

The first sidewall passageway and the second sidewall passageway can define lumens in the shaft section sidewall. Alternatively, the first sidewall passageway and the second sidewall passageway are channels formed in the shaft sidewall. A transition piece can extend partially into the shaft portion and partially into the steering portion. In one embodiment, the transition piece defines spaced-apart, longitudinally extending slots on diametrically opposed sides of the transition piece.

In another embodiment of the disclosure, a method of deflecting a distal tip of a catheter is described. The method comprises:

provi ding a catheter assembly including a shaft portion and a steering portion that define a central axis, the catheter assembly including a first pull wire portion and a second pull wire portion;

within the shaft portion, routing the first pull wire portion and the second pull wire portion proximate the central axis;

within the steering portion, routing the first pull wire portion and the second pull wire portion parallel to and radially offset from the central axis, the first pull wire portion being rotationally offset from the second pull wire portion within the steering portion, causing a neutral axis of the catheter assembly to align substantially with the central axis throughout the shaft portion and the steering portion during actuation of the second pull wire portion; and causing the neutral axis of the catheter assembly to substantially coincide with the first pull wire portion along a proximal portion of the steering section when the first pull wire portion is actuated, the neutral axis being substantially aligned with the central axis at locations proximal to and distal to the proximal portion of the steering section.

BRIEF DESCRIPTION OF THE DRAWINGS

The disclosure may be more completely understood in consideration of the following detailed description of various embodiments in connection with the accompanying drawings, in which.

DETAILED DESCRIPTION

Figure 1:
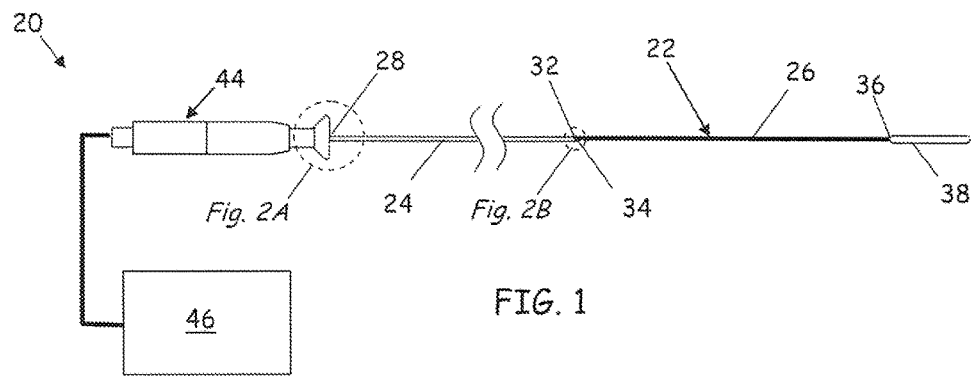
FIG. 1 is a schematic of a catheter system in an embodiment of the disclosure.

Referring to FIG. 1, a catheter system 20 is depicted in a disclosed embodiment. The catheter system 20 comprises an elongated catheter assembly 22 having a shaft portion 24 and a steerable distal portion 26. The shaft portion 24 includes a proximal end 28 and a distal end 32. The steerable distal portion 26 includes a proximal end 34 and a distal end 36, with the proximal end 34 coupled with the distal end 32 of the shaft portion 24. The catheter assembly 22 can also include an end effector 38.

The catheter assembly 22 further comprises at least one pull wire 42 (depicted in the various figures), providing two pull wire portions 42a and 42b operatively coupled to the steerable distal portion 26. Applying a pulling force to one of the at least one pull wires 42 causes steerable distal portion 26 to deflect laterally.

The shaft portion 24 can be operatively connected to a control handle 44 for manipulating the pull wire portions 42a and 42b. The control handle 44 can be operatively coupled with a controller 46 containing various appurtenances that augment the operation of the catheter system 20. Handles for the manipulation of the pull wire portions are disclosed, for example, at U.S. Patent Application Publication No. 2011/0251554 to Romoscanu, at U.S. patent application Ser. No. 13/842,349 to Romoscanu et al., filed Mar. 15, 2013, and at U.S. Patent Application No. 61/817,661 to Romoscanu, filed on Apr. 30, 2013, the disclosures of which are owned by the owner of the instant application and which are incorporated by reference herein in their entirety except for express definitions contained therein. It is understood that any control handle suitable for actuation of the two pull wire portions 42a and 42b can be implemented in the catheter system 20.

In another example, end effector 38 can be fitted with an ablation head coupled to an energy source (not depicted). The energy source can be located within the controller 46. In some embodiments, controller 46 can include analog electronic components to execute the control logic required to monitor operational parameters.

Figure 2A:
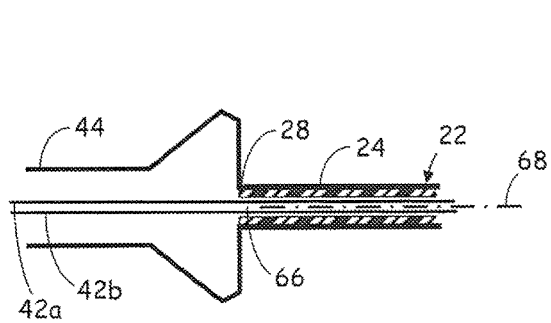
FIGS. 2A through 2C are an enlarged partial sectional views of the catheter system of FIG. 1, according to an embodiment of the disclosure.
Figure 2C:
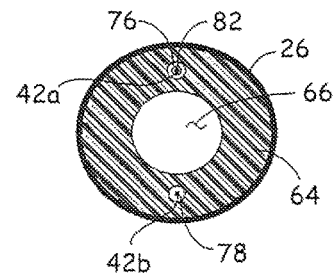
Figure 2B:
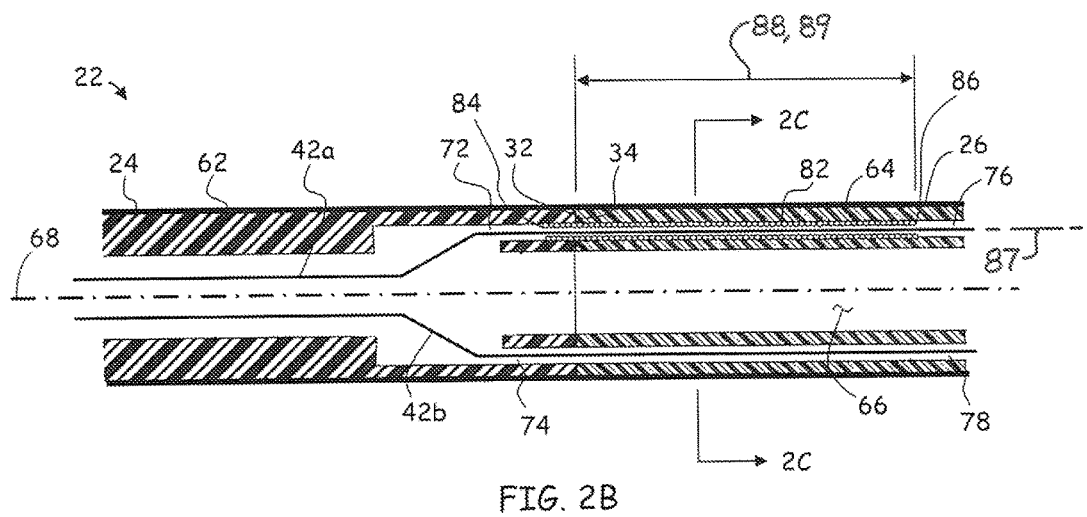

Referring to FIGS. 2A through 2C, views of the catheter assembly 22 are depicted in a disclosed embodiment. In one embodiment, the shaft portion 24 includes a shaft section sidewall 62 and the steering portion 26 includes a steering section sidewall 64 that together define a central lumen 66 and a central axis 68 extending through shaft portion 24 and the steering portion 26. The shaft portion 24 can include first and second shaft sidewall lumens 72 and 74 formed in the shaft section sidewall 62 that extend parallel to the central axis 68 over at least a portion of the length of the shaft portion 24 and passing through the distal end 32 of the shaft portion 24.

In one embodiment, the steering portion 26 can include first and second steering section sidewall lumens 76 and 78 formed in the steering section sidewall 64 that extend parallel to the central axis 68 over the entire length of the shaft portion 24 and passing through the distal end 36 of the steering portion 26.

The first shaft sidewall lumen 72 is rotationally offset from the second shaft sidewall lumen 74 relative to the central axis 68. In the depicted embodiment, the rotational offset is 180°, i.e., the first and second shaft sidewall lumens 72 and 74 are diametrically opposed to each other. Likewise, the first steering section sidewall lumen 76 is rotationally offset from the second steering section sidewall lumen 78 in the same manner, such that the first shaft sidewall lumen 72 is in axial alignment with the first steering section sidewall lumen 76 and the second shaft sidewall lumen 74 is in axial alignment with the second steering section sidewall lumen 78.

A compression coil 82 having a proximal end 84 and a distal end 86 can disposed in the first steering section sidewall lumen 76. The compression coil 82 can be disposed within the first steering section sidewall lumen 76 to define a uni-directional bending portion 89. The uni-directional bending portion 89 is characterized as having a standoff length 88 defined between the proximal end 34 of the steering section 26 and the distal end 86 of the compression coil 82. The compression coil 82 defines an offset axis 87 that, within the uni-directional bending portion 89, is substantially parallel to and radially offset from the central axis 68 of the catheter assembly 22. In one embodiment, the compression coil 82 also extends into the first shaft sidewall lumen 72.

In the depicted embodiment, the first and second pull wire portions 42a and 42b are routed from the handle 44 into the central lumen of the shaft portion 24. Near the distal end 32 of the shaft portion 24, the first and second pull wire portions 42a and 42b are routed into the first and second shaft sidewall lumens 72 and 74, respectively, where they pass through the first and second steering section sidewall lumens 76 and 78, respectively. The first pull wire portion 42a also passes through the compression coil 82.

Figure 3A:
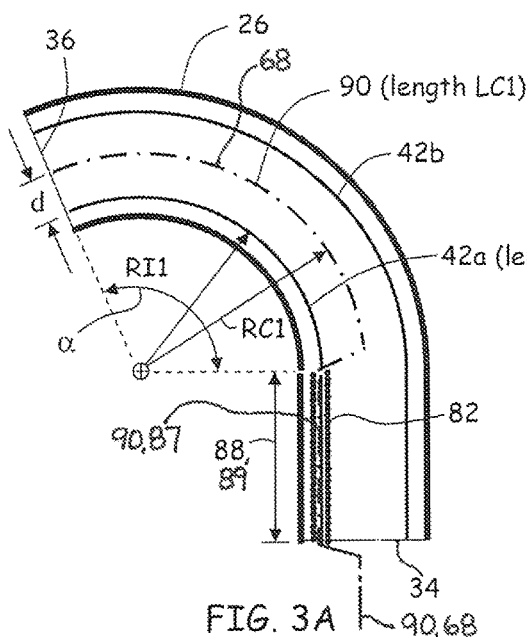
FIG. 3A is an enlarged sectional schematic of a tip deflection with a compression coil in compression in an embodiment of the disclosure.
Figure 3B:
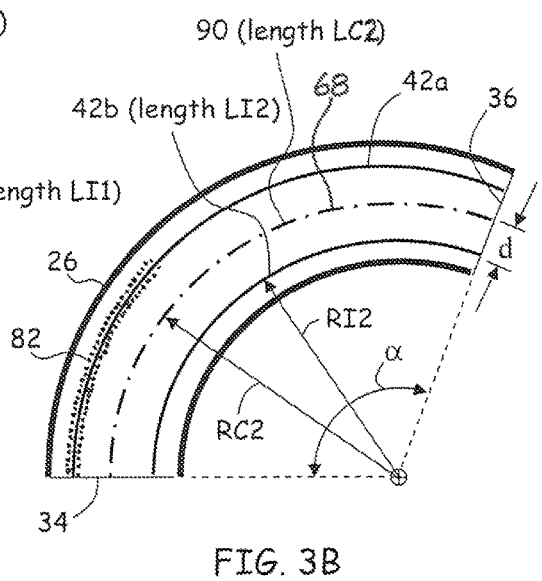
FIG. 3B is an enlarged sectional schematic of a tip deflection with the compression coil in expansion in an embodiment of the disclosure.

Referring to FIGS. 3A and 3B, a formulation of the bending at the distal end 36 of the steering portion 26 of the catheter assembly 22 is depicted in a disclosed embodiment. The FIG. 3A depiction illustrates an actuation of the first pull wire portion 42a by an axial displacement ΔL, whereas FIG. 3B illustrates an actuation of the second pull wire portion 42b by the same axial displacement ΔL. The equations for quantifying the various parameters for the flexing operation are as follows:

$$LCi = RCi \cdot \alpha \qquad \text{Eq. (1)}$$

$$LIi = RIi \cdot \alpha \qquad \text{Eq. (2)}$$

$$d = RCi \cdot RIi \qquad \text{Eq. (3)}$$

$$\Delta Li = LCi \cdot LIi = RCi \cdot \alpha - (RCi - d) \cdot \alpha = d \cdot \alpha => \alpha = \Delta Li/d \qquad \text{Eq. (4)}$$

$$RCi = LCi/\alpha = (LCi/\Delta Li) \cdot d \qquad \text{Eq. (5)}$$

where:
LC=length of the arc bow along the central axis
RC=bend radius of the arc bow along the central axis
LI=Length of the arc bow of the actuated pull wire portion along the sidewall lumen
RI=Radius of the arc bow of the actuated pull wire portion along the sidewall lumen
ΔL=axial displacement of the actuated pull wire portion
α=steering angle
d=radial distance between neutral axis and sidewall lumen
i=1 or 2 (suffix indicating bend direction 1 or bend direction 2)

From Eq. 4, the steering angle α depends on the axial displacement ΔLi of the actuated pull wire and the radial distance d. However, from Eq. (5), the bend radius RCi depends on the steering arc length LCi and the angle α, or the axial displacement ΔLi and the radial distance d. Thus, for a given axial displacement ΔLi, the same steering angle αi is provided, independent of the steering arc length LCi, but the bend radius RCi is influenced by the steering arc length LCi.

In the depicted embodiment, actuation of the pull wire portion 42a or 42b does not impart an appreciable bend radius on the shaft portion 24 because of the passage of the pull wire portions 42a, 42b through the central lumen 66. That is, because the pull wire portions 42a and 42b are close to the central axis 68 in the shaft portion 24, which is also the neutral axis of the shaft portion 24, the actuation axis of the pull wire portions 42a and 42b and the (neutral) central axis 68 are closely aligned over essentially all of the length of the shaft portion 24 (i.e., small "d" value), so that the shaft portion 24 does not undergo a significant deflection.

Figure 4:
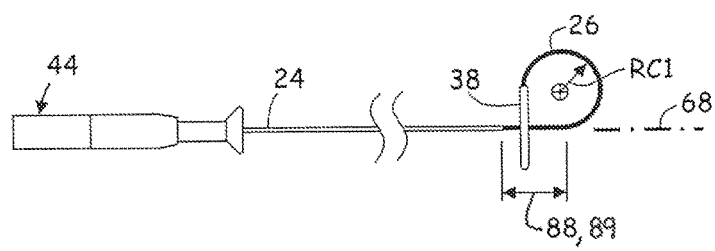
FIG. 4 is a schematic of a catheter system with the compression coil in compression in an embodiment of the disclosure.
Figure 5:
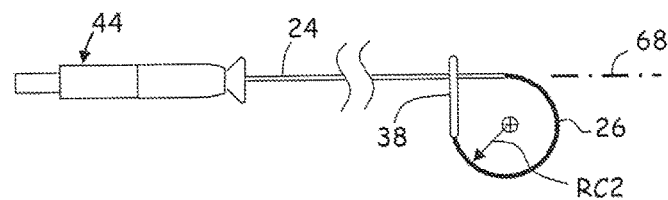
FIG. 5 is a schematic of a catheter system with the compression coil in expansion in an embodiment of the disclosure.

Referring to FIGS. 4 and 5, operation of the catheter assembly is depicted in a disclosed embodiment. Functionally, the compression coil 82 introduces an asymmetry that effectively reduces the steering arc length LC1 of FIG. 3A by the standoff length 88 of the compression coil into the steering portion 26. During actuation of the first pull wire portion 42a (i.e., on the side of the catheter assembly 22 having the compression coil 82), a neutral axis 90 becomes coaxial with the first pull wire portion 42a over the length of the compression coil 82 (FIG. 3A). Thus, when pull wire portion 42a is actuated, the neutral axis 90 lies proximate the central axis 68 at axial locations proximal to and distal to the compression coil 82; however, the neutral axis 90 shifts to be substantially coincident with the offset axis 87 over the length of the compression coil 82 (FIG. 3A).

This shifting of the neutral axis 90 effectively eliminates the standoff length 88 from LC1, which, in accordance with the mathematical descriptions of Eqs. (1) through (4), causes a smaller bend radius RC1 than would be realized absent the shift of the neutral axis 90. Also from Eqs. (1) through (4), while the bend radius RC1 is reduced by the reduction in LC1, the steering angle α remains the same as if there were no shift in the neutral axis. Accordingly, the presence of the compression coil 82 causes a reduction in the bend radius RC1 while not affecting the steering angle α.

In contrast, during actuation of the second pull wire portion 42b, which passes through the second sidewall lumen 78, the neutral axis 90 remains proximate the central axis 68 over the length of the catheter shaft 24 and steering section 26 (FIG. 4B). That is, there is no shift of the neutral axis or attendant reduction in the length of LC2. Furthermore, because the compression coil 82 can be laterally deflected and/or extended, so that the compression coil 82 does not inhibit bending of the steering section during actuation of the second pull wire portion 42b. In accordance with the mathematical descriptions of Eqs. (1) through (4), the bend radius RC2 will be greater than the bend radius RC1 while the steering angle α remains the same. Accordingly, the absence of a compression coil causes a larger bend radius RC2 while not affecting the steering angle α.

In various embodiments, the coil 82 is a "compression coil" in which its loops are in contact with neighboring loops such that the coil behaves like a rigid tube when loaded on compression. The compressibility of the coil relative to the steering shaft material has a ratio of at least 1:5 in various embodiments. In such embodiments, at equal compression loads, the coil 82 deforms in compression by at least five times less than the surrounding steering shaft. In general, the coil should be as weak as possible in extension. As for tension loads, in certain embodiments, the coil can extend by five times more than the steering shaft extrusion under equal loads, to provide the desired level of compliance. Coil dimensions can vary. In one embodiment, the coil can have an outer diameter of 0.42 mm, an inner diameter of 0.26 mm, and be formed of a 0.003 inch by 0.010 inch rectangular section wire stainless steel. In one embodiment, the assembly is designed so that the outer diameter of the coil 82 does not delaminate from the inner diameter of the sidewall lumen 76.

Although a compression coil is disclosed in this embodiment, other uni-directional stiffening members can be utilized as well. A "uni-directional stiffening member" is a device that is rigid in compression and compliant in bending. A compression coil is considered advantageous as it is also compliant upon extension as well. However, an item which is not compliant in bending only but not in extension could be utilized as well. The neutral axis would be defined by the uni-directional stiffening member when the pull wire in the second lumen is placed under tension. In such a case, a non-infinite, but variable bending radius across the standoff length 88 would be obtained.

A variety of catheter dimensions may be possible for the catheter system discussed in this disclosure. In certain embodiments, an 8 French catheter can be used, although the principles discussed in this disclosure should generally apply to any dimension catheter.

Figure 6A:
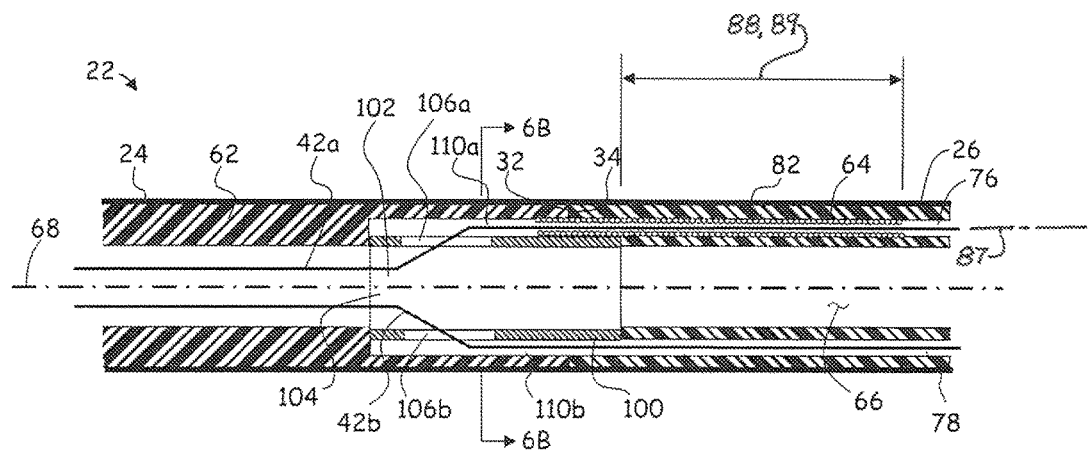
FIG. 6A is an alternate embodiment of the enlarged partial sectional views depicted in FIG. 2B of the catheter system of FIG. 1, according to an embodiment of the disclosure.

Referring to FIG. 6A an alternate arrangement of the enlarged partial sectional view depicted in FIG. 2B of the catheter system 20 is disclosed, according to an embodiment of the disclosure. Specifically, the embodiment shown in FIG. 6A discloses a catheter system including a transition piece 100 proximate the abutment of the distal end 32 of the shaft portion 24 with the proximal end 34 of the steering portion 26. The transition piece 100 is depicted as a generally tubular structure, having a central bore 102 defining a lumen 104 that is axially aligned with the central axis 68 of the catheter system 20. The transition piece 100 also contains spaced-apart, longitudinally extending slots 106a and 106b on diametrically opposed sides of the transition piece 100 that provide passageways from the lumen 104 of the transition piece 100 to the exterior periphery of the transition piece 100. The transition piece 100 extends partially into the central lumen 66 of the shaft portion 24 and partially into the central lumen 66 of the steering portion 26.

Accordingly, embodiments with a transition piece 100, rather than separating the wires to the first and second shaft sidewall lumens 72 and 74 formed in the sides of the shaft portion 24, as in shown in FIG. 2, the transition piece 100 serves as the mechanism by which centrally located pull wire portions 42a and 42b are routed from the central lumen 66 of the shaft portion 24 to the first and second steering section sidewall lumens 76 and 78 disposed within the sidewalls of the steering portion 26. In FIG. 6A, independent first and second shaft sidewall lumens 72 and 74, having entirely separate bores from the central lumen, are not found within the shaft portion 24. Rather, first and second channels 110a and 110b in diametrically opposed sides of the shaft section sidewall are formed over a short axial length at the distal end 32 of the shaft portion 24 to accommodate the pull wire portions 42a and 42b. The channels 110a and 110b are open to the bore of the central lumen along an length of their perimeters. Both the first and second shaft sidewall lumens 72 and 74, as well as the first and second channels 110a and 110b, may be more generally referred to as first and second shaft sidewall "passageways" in this disclosure and claims.

Accordingly, pull wire portions 42a and 42b can be understood to extend from the catheter handle 44, through the central lumen 66 of the shaft portion 24, into the lumen 104 of the transition piece 100. Next, one pull wire portion 42a extends through the slot 106a in one side of the transition piece 100 and the other pull wire portion 42b through the slot 106b in the diametrically opposed wall. The wire portions 42a and 42b are routed against the outer perimeter of the transition piece 100 in the respective channels 110a, 110b in the shaft section sidewalls 62 and into the first and second steering section sidewall lumens 76 and 78 as described above, where one pull wire portion 42a also extends through a compression coil 82.

Figure 6B:
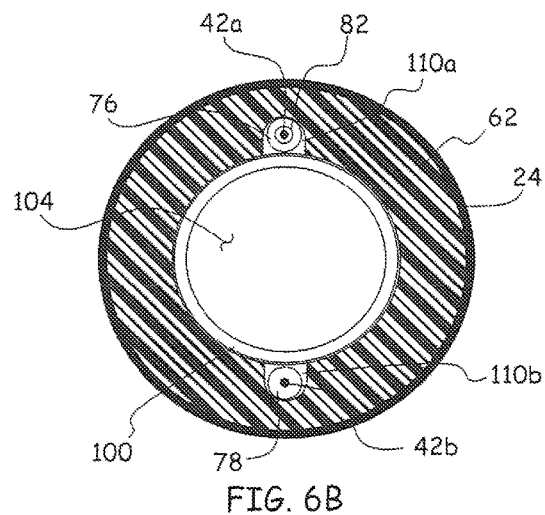
FIG. 6B is an enlarged partial sectional view of the alternate embodiment of the catheter system depicted in FIG. 6A, according to an embodiment of the disclosure.

Referring to FIG. 6B, an enlarged partial sectional view of the embodiment of the catheter system of FIG. 6A is depicted. The cross section of FIG. 6B is taken through the portion of the shaft portion extending over the transition piece 100. Specifically, the cross section is taken through the portion of the distal end 32 on the shaft portion 24, containing channels 110a and 110b in the shaft section sidewall 62, and through the portion of the transition piece that includes slots 106a, 106b. At this axial location, the pull wire portions 42a and 42b are outside the perimeter of the transition piece 100 and within the channels 110a and 110b of the shaft section sidewall 62.

Figure 7:
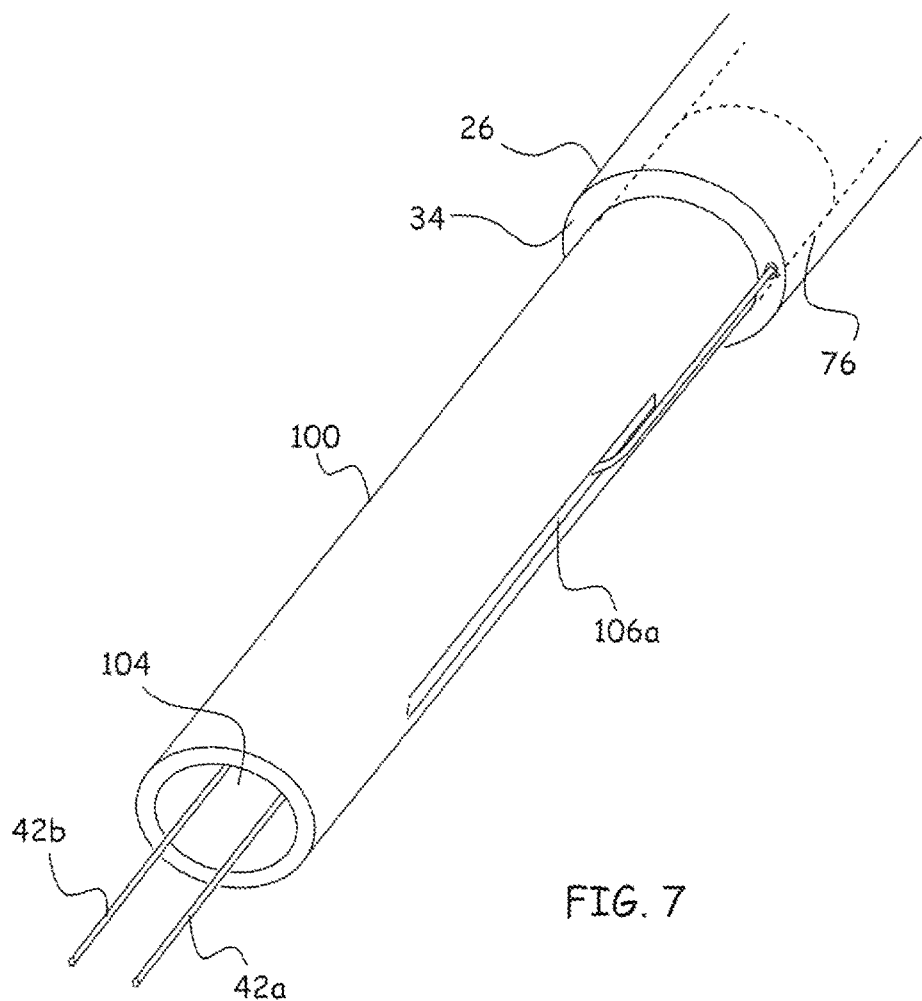
FIG. 7 is a perspective view of the transition piece, pull wire portions and steering portion of the catheter system of FIGS. 6A and 6B with the proximal shaft portion removed according to an embodiment of the disclosure.

Referring to FIG. 7, a perspective view of the transition piece 100, pull wire portions 42a and 42b and the steering portion 26 of the catheter system 20 is depicted based on the embodiments described in FIGS. 6A and 6B. The proximal shaft portion 24 has been removed for clarity in FIG. 7. The pull wire portions 42a and 42b can be seen entering the lumen 104 of the transition piece 100 and the pull wire portion 42a passing through the longitudinal slot 106a of the transition piece 100 and into the first steering section sidewall lumens 76 and 78 of the steering portion 26. The pull wire portion 42b is similarly routed through slot 106b and sidewall lumen 78 (hidden from view in FIG. 7).

Figure 8:
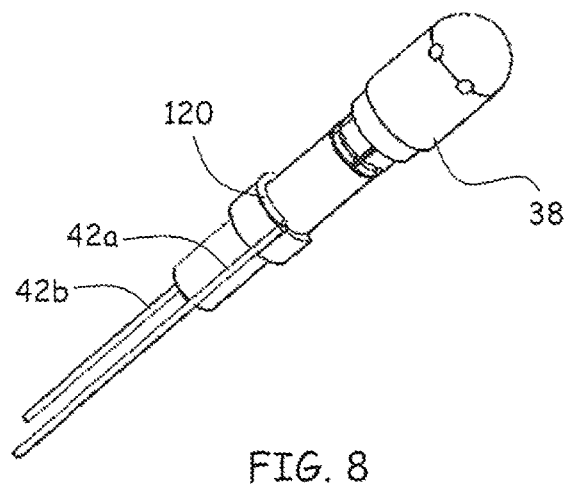
FIG. 8 is a perspective view of the distal end of the steerable distal portion of the catheter system and end effector according to an embodiment of the disclosure.

Referring to FIG. 8, a perspective view of the distal end 36 of the steering portion 26 of the catheter system 20 and end effector 38 is depicted in a disclosed embodiment. The pull wire portion 42 is depicted as forming an end loop 120. The end loop 120 bridges the distal ends of the pull wire portions 42a and 42b at substantially right angles, the end loop 120 conforming to the exterior periphery of one of the sides of the end effector 38. In this way, steering with the single pull portion wire 42 is made possible.

Alternatively, two separate pull wires (not depicted) can be utilized for the pull wire portions 42a and 42b. In this embodiment, the distal ends of the pull wire portions 42a and 42b can be anchored to the end effector 38 by conventional methods (e.g., gluing, welding, or by a ball-and-slot arrangement).

It should also be appreciated that the exemplary embodiment or exemplary embodiments are only examples, and are not intended to limit the scope, applicability, or configuration of the invention in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the invention as set forth in the appended claims and the legal equivalents thereof.

The embodiments above are intended to be illustrative and not limiting. Additional embodiments may be defined within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A catheter assembly, comprising:
    a shaft portion having a proximal end and a distal end and including a shaft section sidewall that defines a central lumen;
    a steering portion having a proximal end and a distal end, said proximal end of said steering portion being operatively coupled with said distal end of said shaft portion, said steering portion including a steering section sidewall having a first steering section sidewall lumen and a second steering section sidewall lumen formed therein, wherein the first and second steering section sidewall lumens are continuous lumens that extend between the steering portion proximal end and the steering portion distal end,
    wherein said catheter assembly defines a central axis that passes through said proximal end of said shaft portion and said distal end of said steering portion, said shaft portion and said steering portion being substantially concentric about said central axis;
    a uni-directional stiffening member operatively coupled to said steering section sidewall proximate said first steering section sidewall lumen and over a standoff length of said steering portion, said uni-directional stiffening member defining a uni-directional bending portion of said steering portion and an offset axis that is radially offset from and substantially parallel to said central axis;
    a first pull wire portion extending through said central lumen and said first steering section sidewall lumen such that actuation of said first pull wire portion causes deflection of said steering portion in a first lateral direction, said first pull wire portion being routed proximate said uni-directional stiffening member,
    wherein during actuation of said first pull wire portion, a neutral axis of said catheter assembly along said uni-directional bending portion is proximate said offset axis such that a first bend radius of said steering portion is defined for a steering angle α; and
    a second pull wire portion extending through said central lumen and said second steering section sidewall lumen such that actuation of said second pull wire portion causes deflection of said steering portion in a second lateral direction,
    wherein during actuation of said second pull wire portion, said neutral axis of said catheter assembly along said uni-directional bending portion is proximate said central axis such that a second bend radius of said steering portion is defined for said steering angle α, said second bend radius being greater than said first bend radius.

2. The catheter assembly of claim 1, wherein said first steering section sidewall lumen is rotationally offset from said second steering section sidewall lumen.

3. The catheter assembly of claim 2, wherein said first steering section sidewall lumen is diametrically opposed to said second steering section sidewall lumen.

4. The catheter assembly of claim 1, wherein a transition piece extends partially into said shaft portion and partially into said steering portion, and wherein the transition piece guides the first and second pull wire portions from the central lumen into respective ones of the first and second steering section sidewall lumens.

5. The catheter assembly of claim 1, wherein said first pull wire portion and said second pull wire portion are two separate pull wires.

6. The catheter assembly of claim 1, wherein said uni-directional stiffening member is a compression coil.

7. The catheter assembly of claim 6 wherein said compression coil has an outer diameter of about 0.42 mm and an inner diameter of about 0.26 mm.

8. The catheter assembly of claim 6, wherein said compression coil does not delaminate from said first steering section sidewall lumen.

9. The catheter assembly of claim 6, wherein a compressibility ratio of said compression coil relative to said steering section sidewall is at least 1:5.

10. The catheter assembly of claim 6, wherein said compression coil is formed of a 0.003 inch by 0.010 inch rectangular section wire.

11. The catheter assembly of claim 1, wherein:
    said shaft section sidewall defines a first shaft sidewall passageway and a second shaft sidewall passageway formed therein, said first shaft sidewall passageway and said second shaft sidewall passageway extending parallel to said central axis over at least a portion of said shaft portion and passing through said distal end of said shaft portion, said first shaft sidewall passageway being axially aligned with said first steering section sidewall lumen, said second shaft sidewall passageway being axially aligned with said second steering section sidewall lumen; and
    said first pull wire portion and said second pull wire portion pass through said first shaft sidewall passageway and said second shaft sidewall passageway, respectively.

12. The catheter assembly of claim 11, wherein said first shaft sidewall passageway and said second shaft sidewall passageway define lumens in said shaft section sidewall.

13. The catheter assembly of claim 11, wherein said first shaft sidewall passageway and said second shaft sidewall passageway are channels formed in the shaft section sidewall.

14. The catheter assembly of claim 13, wherein a transition piece extends partially into said shaft portion and partially into said steering portion.

15. The catheter assembly of claim 14, wherein said transition piece defines spaced-apart, longitudinally extending slots on diametrically opposed sides of the transition piece through which the first pull wire portion and the second pull wire portion extend, respectively.

16. The catheter assembly of claim 1, wherein said second lateral direction is different than said first lateral direction.

17. A method of deflecting a distal tip of a catheter, comprising:
    providing a catheter assembly including a shaft portion, a steering portion, and a transition portion between the shaft portion and the steering portion that define a central axis, said catheter assembly including a first pull wire portion and a second pull wire portion;
    within said shaft portion, routing said first pull wire portion and said second pull wire portion proximate said central axis and through a central lumen defined by the shaft portion;
    within said transition portion, routing said first pull wire portion and said second pull wire portion from the central lumen through longitudinally extending slots defined in the transition portion into steering portion sidewall lumens defined in a sidewall of the steering portion;

within said steering portion, routing said first pull wire portion and said second pull wire portion parallel to and radially offset from said central axis through the steering portion sidewall lumens, said first pull wire portion being rotationally offset from said second pull wire portion within said steering portion, causing a neutral axis of said catheter assembly to align substantially with said central axis throughout said shaft portion and said steering portion during actuation of said second pull wire portion; and causing said neutral axis of said catheter assembly to substantially coincide with said first pull wire portion along a proximal portion of said steering section when said first pull wire portion is actuated, said neutral axis being substantially aligned with said central axis at locations proximal to and distal to said proximal portion of said steering section.

* * * * *